(12) United States Patent
Taub et al.

(10) Patent No.: US 7,104,792 B2
(45) Date of Patent: Sep. 12, 2006

(54) APPLIANCE FOR POSITIONING ORTHODONTIC COMPONENTS

(75) Inventors: Eldad Taub, Reut (IL); Avi Kopelman, Ramat Chen (IL); Israel Shapira, Rosh Ha'avin (IL)

(73) Assignee: Cadent Ltd., Or Yehuda (IL)

( * ) Notice: Subject to any disclaimer, the term of this patent is extended or adjusted under 35 U.S.C. 154(b) by 356 days.

(21) Appl. No.: 10/426,953

(22) Filed: May 1, 2003

(65) Prior Publication Data
US 2003/0215767 A1 Nov. 20, 2003

Related U.S. Application Data

(60) Provisional application No. 60/416,656, filed on Oct. 7, 2002, provisional application No. 60/377,308, filed on May 2, 2002.

(51) Int. Cl.
*A61C 7/14* (2006.01)

(52) U.S. Cl. ............... 433/24; 433/3; 433/29

(58) Field of Classification Search ............ 433/2, 433/3, 8, 9, 24, 29
See application file for complete search history.

(56) References Cited

U.S. PATENT DOCUMENTS

| | | | |
|---|---|---|---|
| 4,850,864 A * | 7/1989 | Diamond | 433/3 |
| 4,915,626 A * | 4/1990 | Lemmey | 433/31 |
| 5,290,168 A * | 3/1994 | Cooper et al. | 433/29 |
| 5,711,665 A | 1/1998 | Adam et al. | |
| 6,200,134 B1 | 3/2001 | Kovac et al. | |
| 6,334,772 B1 | 1/2002 | Taub et al. | |
| 6,482,002 B1 * | 11/2002 | Jordan et al. | 433/9 |
| 6,695,613 B1 * | 2/2004 | Taub et al. | 433/24 |
| 6,743,013 B1 * | 6/2004 | Jordan et al. | 433/9 |
| 6,905,337 B1 * | 6/2005 | Sachdeva | 433/229 |

FOREIGN PATENT DOCUMENTS

| | | |
|---|---|---|
| EP | 0 780 101 | 6/1997 |
| EP | 0 941 691 | 9/1999 |
| FR | 2 656 215 | 6/1991 |
| WO | WO 99/16380 * | 4/1999 |

OTHER PUBLICATIONS

Hansen, Jim, et al., "High Intensity Curing Lights". The Orthodontic CYBERjournal, Dec. 2000.
Gange, Paul, "Orthodontic Bonding". California Association of orthodontics.

* cited by examiner

*Primary Examiner*—Ralph A. Lewis
(74) *Attorney, Agent, or Firm*—Nath & Associates PLLC; Gregory B. Kang; Derek Richmond

(57) ABSTRACT

A positioning appliance adapted to facilitate an orthodontics procedure in which a bracket or other orthodontic component is placed at a desired site on the surface of a tooth and affixed thereto. The appliance comprises a hand-held tubular wand that has a protective sleeve section and a camera section telescoped in the sleeve section. A window is mounted at the front end of the sleeve section and a finger projecting therefrom is adapted to hold the bracket at a position abutting the tooth surface. A camera is housed in the camera section to capture through the window an image of the bracket on the surface of the tooth. One or more light sources are housed in the camera section, for irradiating the bracket and the tooth surface with light detectable by the camera. Additional one or more light sources are housed in the camera section and are capable of irradiates light at a wavelength that can cure an adhesive used for affixing the bracket or other orthodontic component to the surface of a tooth.

47 Claims, 5 Drawing Sheets

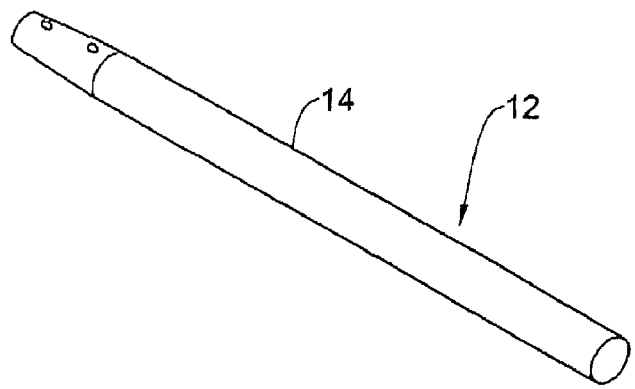
FIG. 7
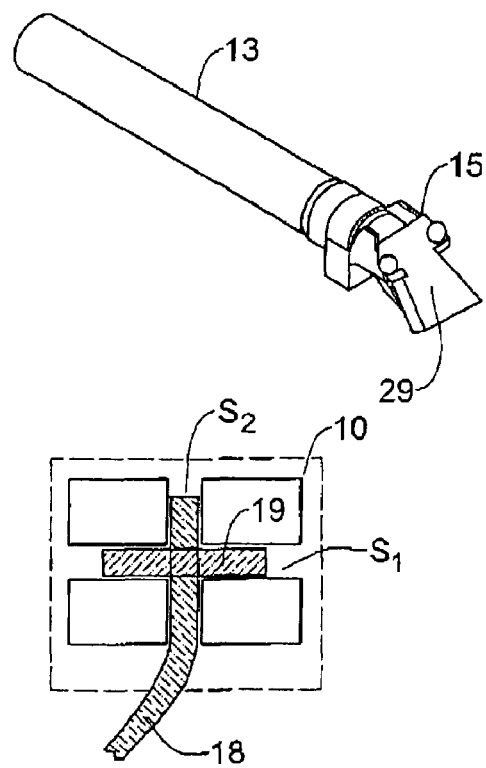
FIG. 8
FIG. 9
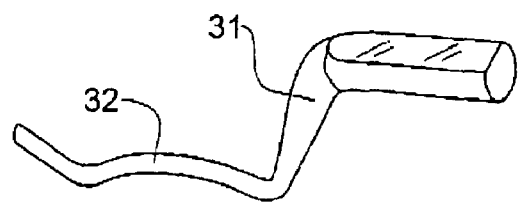
FIG. 10

APPLIANCE FOR POSITIONING ORTHODONTIC COMPONENTS

CROSS REFERENCE TO RELATED APPLICATIONS

This application claims benefit of U.S. Provisional Application 60/377,308 filed on May 2, 2002 and U.S. Provisional Application 60/416,656 filed on Oct. 7, 2002.

FIELD OF THE INVENTION

This invention relates generally to methods for placing a bracket or other orthodontic component on the surface of a tooth of a patient undergoing orthodontic treatment, and to systems and devices for carrying out these methods.

STATUS OF PRIOR ART

Orthodontics is the branch of dentistry dealing with teeth irregularities and their connections, such as by means of braces. The primary purpose of orthodontic treatment is to alter the position and reorient an individual's teeth so as to modify or improve their function. Teeth may also be reoriented mainly for cosmetic reasons.

In orthodontic treatment, as currently practiced, it is necessary to affix various orthodontic components to the surfaces of a patient's teeth. (In this specification, we shall only refer to brackets as the orthodontic component to be anchored on a tooth's surface, but it is to be understood that this is only by way of example.)

Brackets affixed to teeth surfaces serve to support wires and tensioning springs to exert moments of force acting to move the teeth subjected to these forces to a degree and in a direction causing the teeth to assume a desired posture in the dental arch. A typical treatment plan includes, among other factors, the desired position of each of the force-inducing orthodontic implements on the teeth. The placement of the brackets on the teeth determines the outcome of the above-mentioned movements, e.g. the degree and direction of the teeth movements. Any deviation from the planed position of the brackets affects the outcome of the treatment. Thus, during the process of placing the brackets on the teeth, much effort is made to ensure the accurate positioning of the brackets in accordance with their desired position as determined by the treatment plan.

Typically, the following general steps are conducted for properly positioning an orthodontic element such as a bracket on a tooth surface, and then fixing the bracket thereto:

Step I: The orthodontist brings the element, being held by the positioning tool, into proximity of the tooth;

Step II: the orthodontist then positions the orthodontic element on the tooth surface at the site coinciding with its intended position, and disengages it from the positioning tool.

Step III: Finally, the element is affixed to the designated site by a bonding agent.

Typically, the bonding of the bracket to the tooth is achieved by using either chemical adhesives or light curing adhesives. Chemical adhesives are typically cured by themselves. The curing begins as the adhesive coming in contact with the tooth surface is completely cured after some self-working time (typically about 30 seconds). Light curing adhesives are light-sensitive materials, which begin curing after being exposed to curing light of the appropriate wavelength. The strength of bonding is proportional to the amount of energy absorbed by the light-curing adhesive. According to the known orthodontic procedures that utilize light-curing adhesives, as currently practiced, the curing process is conducted by a curing tool, thus compelling the disengagement of the bracket from the positioning tool to accrue befor the curing process is initiated. Typically the curing process is performed by the orthodontist's assistant. U.S. Pat. No. 5,711,665 and U.S. Pat. No. 6,200,134 disclose curing tools. Additional relevant articles are "Orthodontic Bonding" by Paul Gange, published at the California Association of Orthodontics (www.caorto.org/articles/Paul-GangeBonding.htm) and "High Intensity Curing Lights" by Jim Hansen and Brian Lotte from 3M Unitek, at the Orthodontic CYBERjournal (www.oc.j.com.dec00/LIGHT-S.htm).

The difficulty with orthodontic procedures, as commonly practiced nowadays, is that they are manual and as such, subject to human error. A common difficulty relates to the disengagement of the bracket from the positioning tool, as this process typically causes a slight movement of the bracket on the tooth due to inherent and uncontrolled small human movements.

This difficulty is compounded when the orthodontist must place brackets not only on buccal tooth surfaces but also on lingual surfaces. With existing methods, it is not easy for an orthodontist to properly position brackets on lingual surfaces.

These difficulties are obviated in part by methods disclosed in prior U.S. Pat. No. 6,334,772 (2002) to Taub et al. (hereinafter the Taub patent) and the systems and devices disclosed therein to carry out these methods. The entire is disclosure of the Taub patent entitled "Placing an Orthodontic Element on. Tooth Surface" is incorporated herein by reference.

In a preferred method disclosed in the Taub patent, the following steps are conducted for properly positioning an orthodontic element such as a bracket on a tooth surface and then fixing the bracket thereto.

Step I: The orthodontist brings the element into proximity of the tooth while continuously capturing by means of a video camera an image of the tooth or of the element, or both, once the tooth and the element are next to each other;

Step II: The image so captured is conveyed to a video monitor on whose screen is displayed a real-time image, together with indicators affording information in regard to the position intended for the orthodontic element on the tooth surface.

Step III: Guided by these indicators, the orthodontist then positions the orthodontic element on the tooth surface at a site that coincides with its intended position.

Step IV: Finally, the element is affixed to this site by a bonding agent.

In the Taub patent, the positioning appliance to carry out the above-described method includes a mount formed by parallel rails having at their front end a pair of resilient clamping arms which grip the bracket to be positioned. Extending rearwardly from the rear end of this mount is a handle. Supported on the mount is a video camera optically trained on the gripped bracket to provide a video image of the bracket and of the surface of the tooth on which it is placed.

This image is conveyed to an external video monitor and is displayed on its screen which is viewed by the user of the appliance whereby as the user manipulates the appliance to shift the position of the bracket on the tooth surface, he can at the same time observe the changing position of the bracket and be guided thereby.

The hand-held positioning appliance shown in the Taub patent is capable of carrying out die various methods disclosed therein. However, the appliance has practical limitations that may interfere with its effective use.

The handle of the Taub appliance extends from its rear end which is distant from the bracket to be placed on the tooth surface, which bracket is held at a position ahead of the front end of the appliance. When manipulating this appliance to shift the position of the bracket on the tooth surface, in some instances the operator would have better control of the appliance if it were grasped at a position closer to its front end than to its rear end. But this is not feasible when the handle, as in the Taub patent appliance, projects beyond its rear end.

Another shortcoming of Taub's positioning appliance is that its video camera which is optically trained on the bracket held ahead of its front end is unshielded and therefore exposed to ambient light. This light, to the extent that it is admitted into the camera, acts to cloud the video image of the bracket and adjacent tooth surface.

But the more consequential drawback of the Taub appliance is the difficulties which arise when seeking to repeatedly use the appliance to perform subsequent treatments.

In order for an appliance that makes physical contact with a patient to be useable, the portion thereof which engages the patient must be of a medically acceptable material. Thus a suitable material in the case of an orthodontics appliance is stainless steel or titanium, for these materials do not react chemically with fluids present in the oral cavity. Moreover, the contact portion of the orthodontics appliance must be sterile when put to use. But when the appliance is used, the portion making contact with the patient becomes contaminated; hence before the appliance can be re-used, it must be again rendered sterile.

One cannot in the case of an appliance of the Taub type simply put the appliance in a dental autoclave in which it will be subjected to superheated steam under high pressure. To do so would ruin the costly miniature video camera as well as electronic and other components associated with the camera. Hence in order to sterilize the Taub appliance, it has to be disassembled so that only the mount of the appliance is put into the autoclave, after which it becomes necessary to reassemble the appliance.

A typical orthodontist makes frequent use of an appliance to position orthodontic components and is therefore discouraged from using an appliance that cannot be expeditiously sterilized even though the appliance aids him to properly place orthodontic components on tooth surfaces.

SUMMARY OF THE INVENTION

In view of the foregoing, the main object of this invention is to provide a band-held appliance adapted to facilitate an orthodontics procedure in which a bracket or other orthodontic component is positioned on the surface of a patient's tooth and affixed thereto at a desired site.

A salient feature of an appliance according to the present invention is that it is the form of a tubular wand. This wand lends itself to easy manipulation, for it can be grasped by the orthodontist like a writing pen at whatever position along its length affords a mechanical advantage appropriate to the existing position of the bracket as it is being shifted on the surface of the tooth toward a desired site thereon.

More particularly, an object of this invention is to provide an appliance in a tubular wand format having a video camera section which telescopes into a sleeve section having at its front end a window and a projecting finger which supports the bracket so as to place it ahead of the window whereby the camera can be trained on the bracket to capture a video image of the bracket and the tooth surface on which it is shiftable.

A significant advantage of a positioning appliance in which a video camera section is telescoped into a protective sleeve section and is removable therefrom is that it is only the sleeve section that makes physical contact with the body of the patient and is contaminated thereby. Hence before reusing the appliance, it is only necessary to detach the camera section and then safely sterilize the sleeve section. Hence an appliance in accordance with the invention can expeditiously be put in condition for repeated use.

An appliance in accordance with the invention comes in two main embodiments, one best adapted to apply a bracket or other orthodontic component to the buccal tooth surfaces, the other to lingual tooth surfaces. It is no more difficult with this appliance to affix a bracket to a lingual surface than to a buccal surface.

A further object of this invention is to provide an appliance for positioning on a tooth surface a bracket whose rear face is cross-slotted, the appliance including a finger whose tip is shaped to wedge into a slot of the bracket whereby the bracket is firmly held by the finger and is not dislodged therefrom as the bracket is shifted on the tooth surface.

Yet another object of this invention is to provide an appliance for positioning a bracket on a tooth's surface such that the bracket is disengaged from the appliance when it is secured to its position on the tooth surface.

Briefly stated, these objects are accomplished in a positioning appliance formed by a tubular wand provided with a protective sleeve section at whose front end is a window and a finger projecting therefrom to hold a bracket at a position abutting the surface of the tooth to which the bracket is to be affixed, and a video camera section having a light source telescoped in the sleeve section adapted to capture through the window an illuminated image of the bracket and the tooth surface.

The video image yielded by the camera section is conveyed to an external monitor on whose screen is displayed in real time the video image of the bracket as it is being manipulated by the user of the appliance so that by observing the screen, the user can see how to shift the bracket toward its desired site on the tooth surface.

The protective sleeve section is formed of sterilizable material which becomes contaminated when the appliance is put to use and makes contact with the body of the patient. To reuse the appliance it is only necessary to detach the camera section from the sleeve section and sterilize the sleeve section.

According to one embodiment, the invention provides a positioning appliance adapted to facilitate an orthodontic procedure in which a bracket or other orthodontic component is placed at a desired site on the surface of a tooth and affixed thereto. The appliance comprises a hand-held tubular wand that has a protective sleeve section and a camera section telescoped in the sleeve section. A window is mounted at the front end of the sleeve section and a finger projecting therefrom is adapted to hold the bracket at a position abutting the tooth surface. A camera is housed in the camera section to capture through the window an image of the bracket on the surface of the tooth. One or more light sources are housed in the camera section, for irradiating the bracket and the tooth surface with light detectable by the camera. Additional one or more light sources are housed in the camera section and are capable of irradiating light at a wavelength that can cure an adhesive used for affixing the bracket or other orthodontic component to the surface of a tooth.

According to yet another embodiment, the invention provides a positioning appliance adapted to facilitate an orthodontic procedure in which a bracket or other orthodontic component is placed at a desired site on the surface of a tooth and affixed thereto. The appliance comprises a hand-held tubular wand that has a protective sleeve section and a light source section, which is telescoped in the sleeve section. A window is mounted at the front end of the sleeve section and a finger projecting therefrom is adapted to hold the bracket at a position abutting the tooth surface. One or more light sources are housed in the light source section, and are capable of irradiating light at a wavelength that can cure an adhesive used for affixing said bracket or other orthodontic component to said surface of a tooth.

BRIEF DESCRIPTION OF THE DRAWINGS

For a better understanding of the invention as well as other objects and features thereof, reference is made to the annexed drawings wherein:

FIG. 7 shows the reflector-view appliance with its camera section withdrawn from its sleeve section;

FIG. 8 illustrates a finger included in an appliance according to the invention for holding a bracket to be placed on a tooth surface, the finger having a wedge-shaped tip adapted to wedge into a slot on the rear face of the bracket;

FIG. 9 shows the wedge-shaped tip wedged into a bracket slot;

FIG. 10 illustrates a finger tip in the form of an arched wire adapted to engage a slot in the bracket;

DETAILED DESCRIPTION OF THE INVENTION

Direct-View Appliance: Shown in FIGS. 1 to 5 is a direct view appliance 12 for positioning an orthodontic bracket 10 or other component on the front face of a tooth 11 so that it occupies a desired site on the surface appropriate to the orthodontics procedure to which a patient is being subjected.

Appliance 12 serves to hold bracket 10 against the tooth surface and to shift its position thereon to a desired site at which it is then affixed to the tooth surface. It is important therefore that the bracket be exactly placed at the desired site before it is bonded to the tooth surface, for once the bracket is affixed, it cannot be shifted to correct its position.

Hence the bonding agent must be such as to allow shifting of the bracket until it occupies the desired site. Preferred agents for this purpose are chemical adhesives and light sensitive adhesives which are activated only when exposed to high intensity light or an ultraviolet beam. The bonding agent is normally in a fluidic state to permit the bracket to shift, the agent being cured and rigidified only at the instant it is activated.

Figure 1:
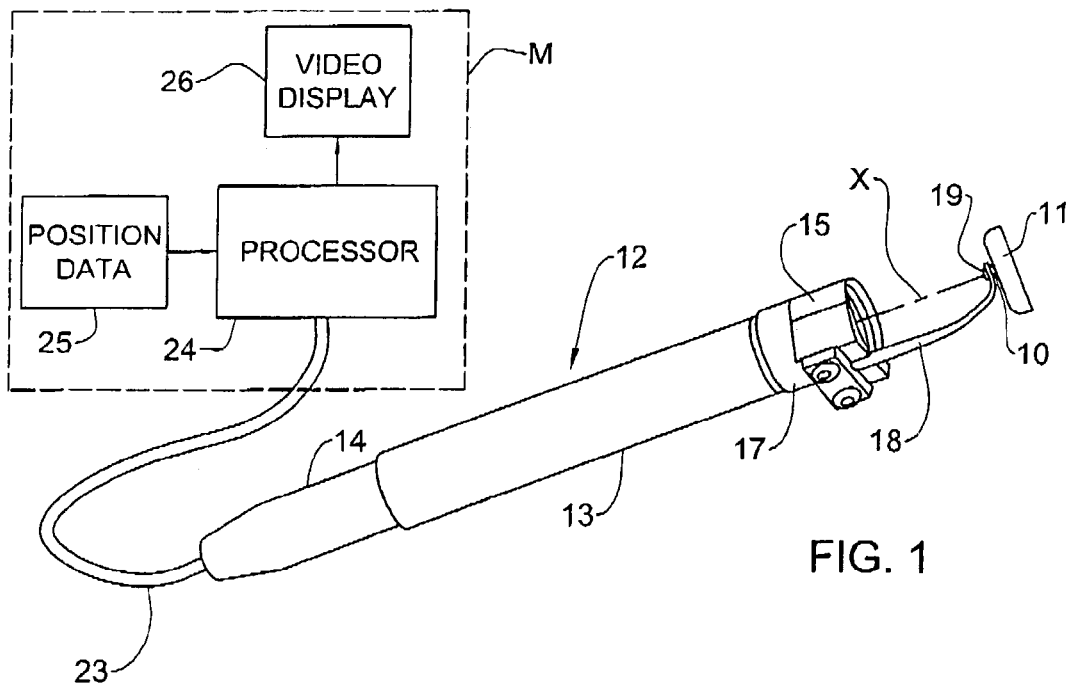
FIG. 1 illustrates in perspective a direct-view appliance in accordance with an embodiment of the invention adapted to position an orthodontic bracket or other implement on a tooth surface, the appliance being associated with an external video monitor.
Figure 2:
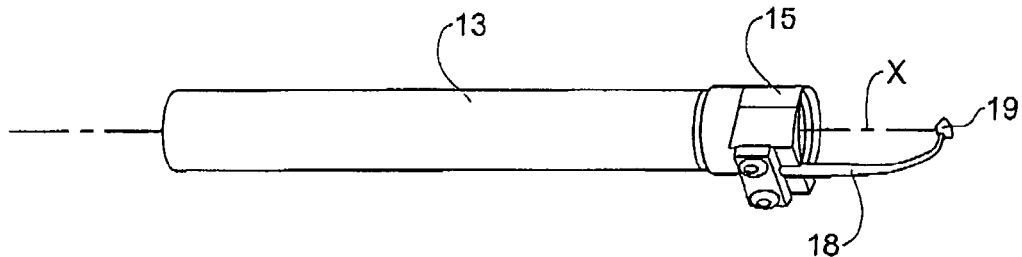
FIG. 2 separately shows the sleeve section of the appliance of FIG. 1.
Figure 3:
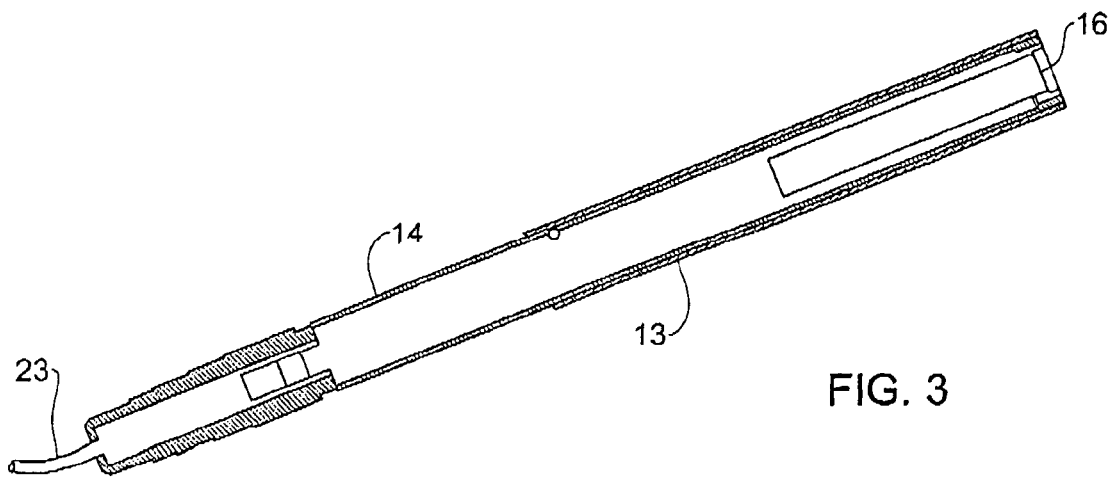
FIG. 3 separately shows the video camera section of the appliance of FIG. 1.

Appliance 12 is in the form of a hand-held tubular wand composed of a protective sleeve section 13 and a video camera section 14 telescoped into the sleeve section as shown in FIGS. 1 and 3. Hence the overall length of the appliance is that attained when the camera section is fully telescoped within the sleeve section.

Sleeve section 13 must be fabricated of a medically acceptable material that can be sterilized in a dental autoclave or other sterilizer where it is subjected to extremely high temperatures. Suitable for this purpose is a stainless steel or titanium tube. Sleeve section 13 is provided at its front end with a collar 15 supporting a window 16 to admit light into and out of the appliance. Secured to collar 15 by a holding plate 17 is a curved finger 18 which projects from the front end of the appliance and terminates in a tip 19 that firmly engages bracket 10 to hold it against the surface of tooth 11. The curvature of finger 18 is such as to place its tip 11 in line with the optical axis X of the appliance, which axis is coaxial with tubular sleeve section 13.

Figure 4:
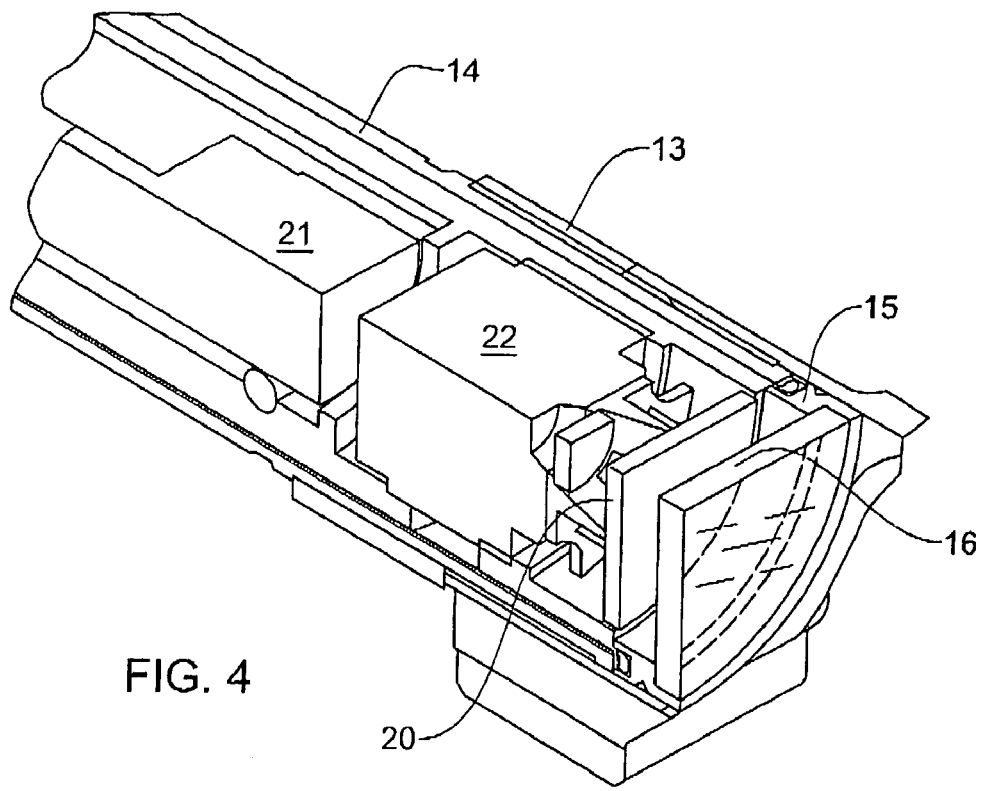
FIG. 4 shows the array of LED lights adjacent the front end of the camera section of the appliance of FIG. 1, which produces a light beam to illuminate the bracket in front of the sleeve section and the tooth surface engaged thereby.
Figure 5:
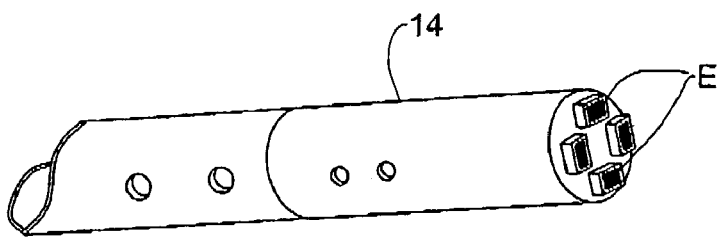
FIG. 5 is a longitudinal section of the camera section of the appliance of FIG. 1 exposing the video camera and the elements associated therewith which are represented in block form.

Camera section 14, as seen in FIG. 4, is provided with a light housing 20 which as shown in FIG. 5 supports a circular array of LED light emitters E to produce a beam of light which is projected through window 16 at the front end of sleeve section 13 to illuminate bracket 10 in line with optical axis X of the appliance and the tooth surface behind the bracket.

Also housed in camera section 14 is a miniature video camera module represented by block 21, such as a CCD unit, and a lens represented by block 22 which focuses an incoming image of the illuminated bracket and tooth surface 11 onto the video camera. Thus the video camera generates a changing image of the bracket as it is being shifted by the appliance toward the desired site on the tooth surface.

The image captured by video camera section 14 is conveyed by a cable 23 extending from the rear end of this section to an external video and processing monitoring station M similar to that disclosed in the Taub patent. In this station, the image captured by the video camera of the appliance is fed into a microprocessor 24 into which is also fed proper bracket position information from a computer 25. The processor transfers this image and information to a video display 20 which in real time shows on its screen both the changing image as the appliance is being manipulated and the position information which guides the user.

Thus a user when manipulating the appliance can see what he is doing by observing the display and is guided thereby by the information on the screen as to just where to shift the bracket on the tooth surface so that its position coincides with the desired site on the tooth surface.

Because the user can grasp the appliance wand at any position along its length, he can select that position which provides him with an optimum mechanical advantage. Thus when the appliance has brought the bracket close to its desired site, the wand is then best held at a position near its front end so that the user can effect fine control of the bracket position.

Figure 6:
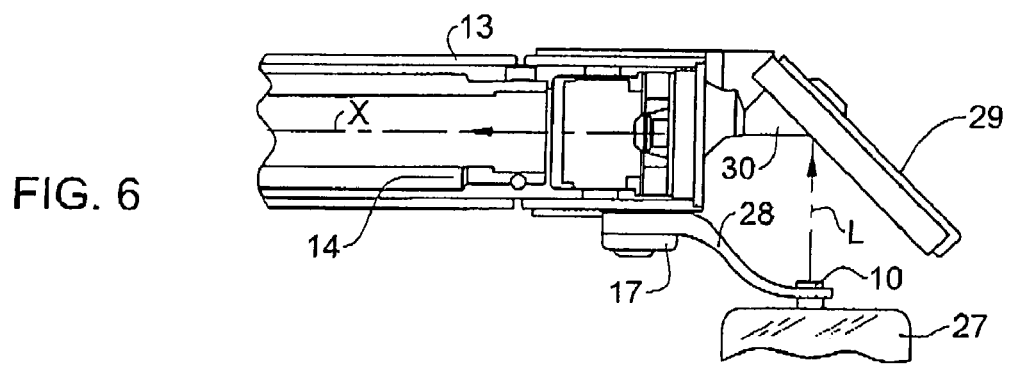
FIG. 6 is a section taken through the sleeve section of a reflector view appliance in accordance with the invention.

Reflector-view appliance This appliance which is illustrated in FIGS. 6 and 7 is best adapted to position bracket 10 on the surface of a tooth 27 lying in a plane parallel to optical axis X coaxial with sleeve section 13 and normal to a lateral axis L which, as shown in FIG. 6, is perpendicular to optical axis X.

Because of the tooth position, it cannot be directly viewed by the camera section 14. Bracket 10 is held against the surface of tooth 27 by a curved finger 28 at a position that is offset with respect to optical X. Hence in order for video camera 21 in the camera section 14 telescoped in sleeve section 13 to see an image of the bracket and of the tooth surface, this image must by reflection be directed into the appliance. To this end, a reflector 29 is provided at the intersection of optical axis X and lateral axis L. Reflector 29 which preferably is formed by a metal plate having a specular surface, is supported by a bracket 30 mounted at the front end of sleeve section 13 at a 45 degree angle to the optical axis.

In all other respects the structure and operation of the reflector-view appliance is the same as that as the direct view appliance.

Bracket holding Fingers: It is essential for proper operation of the appliance that the finger projecting from the front end of the sleeve section and holding the tiny bracket to be positioned firmly hold the bracket so that it does not alter its position on the tip of the finger as the bracket is being shifted on the tooth surface.

To this end FIGS. 8 and 9 illustrate the finger 18 shown in FIG. 1 whose finger tip 19 is wedge-shaped so that it can be pressure-wedged into a slot in the cross-slotted rear face of bracket 10. As shown in FIG. 9, the cross-slotted rear face is defined by a horizontal slot $S_1$ intersecting a vertical slot $S_2$.

As shown in FIG. 8, the free end portion of finger 18 is received in a bore in the center of the wedge-shaped tip 19. Hence to attach the tip to the bracket 10 the wedge is pressed into slot $S_1$ and the end portion of finger 18 is nested in slot $S_2$ to maintain the bracket securely attached to the finger as the appliance is being manipulated. It is a simple matter to couple the finger to the bracket, for it is only necessary to press the finger tip into the slotted cross.

In the finger 31 shown in FIG. 10, its tip is defined by an arched wire 32 adapted to wedge into a slot at the rear face of the bracket. The dimension of the arch relative to that of the slot is such that when the arch is pressed into the slot, axial displacement of the bracket is resisted.

Illuminating system: as described above, the positioning appliance is provided with an illuminating system. (block 20 in FIG. 1) for irradiating the bracket and the tooth surface with light that is detected by the video camera. In another positioning appliance according to the invention, the illuminating system is further configure to irradiate light at a wavelength that can cure an adhesive used for affixing the bracket to the tooth surface. Such an illuminating system can be implemented in the direct-view embodiment as well as in the Reflector-view embodiment.

Figure 11:
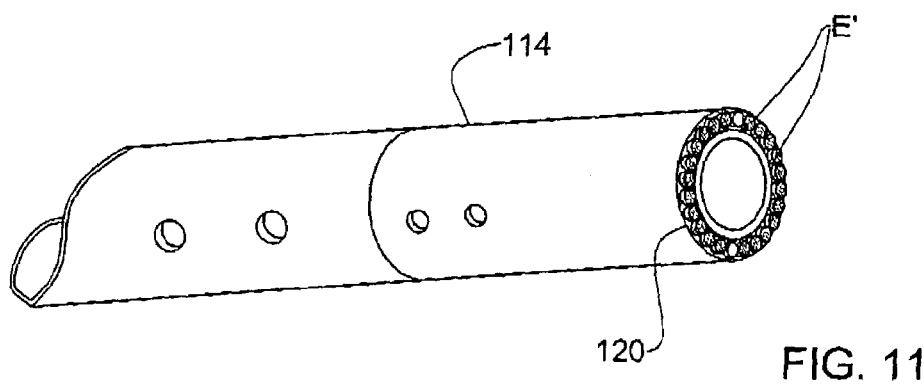
FIG. 11 is a longitudinal section of the camera section according to an embodiment of the invention, showing the light source elements.
Figure 12:
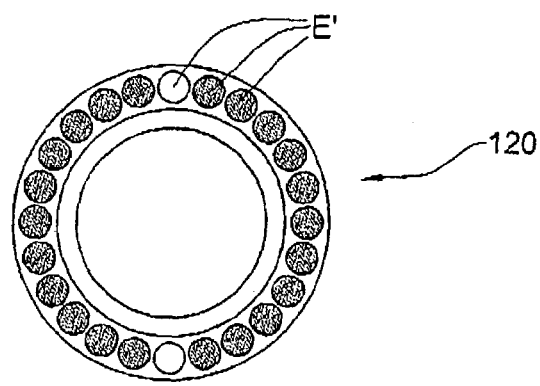
FIG. 12 is a front view of the camera section of FIG. 11.
Figure 13:
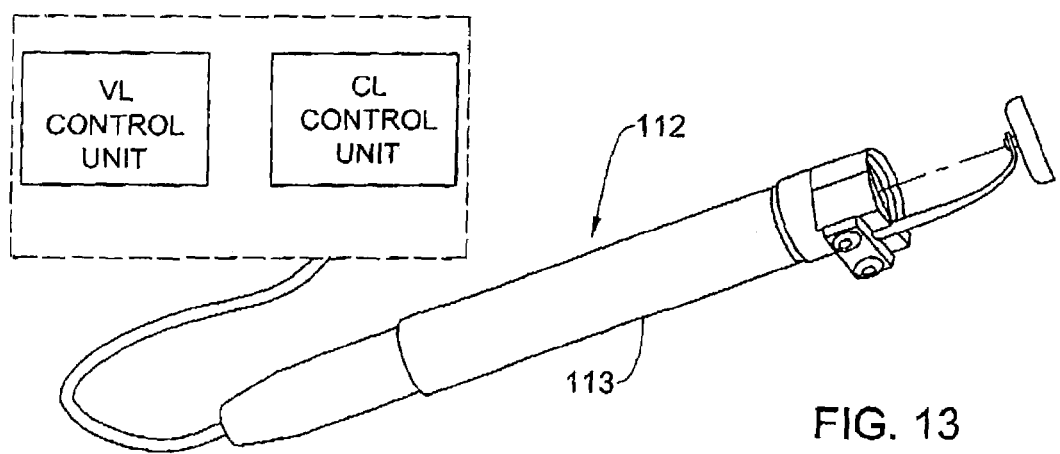
FIG. 13 illustrates in perspective a direct-view appliance in accordance with an embodiment of the invention adapted to position an orthodontic bracket or other implement on a tooth surface, the appliance being associated with an external video monitor and capable of affixing the bracket or other implement to the tooth surface.

Reference is now drawn to FIGS. 11–13. The appliance 112 is adapted to position an orthodontic bracket or other implement on a tooth surface and is capable of affixing the bracket or other implement to the tooth surface. According to this embodiment the bonding between the bracket and the tooth surface is achieved by using a light sensitive adhesive. The camera section 114 is provided with a light housing 120 which supports a circular array of LED light emitters E' (also shown in FIG. 12) to produce a beam of light which is projected to illuminate the bracket and the tooth surface behind the bracket. Also housed in camera section 114 is a miniature video camera module and, a lens (both not shown in FIG. 11) which focuses an incoming image of the illuminated bracket and tooth surface onto the video camera. Section 114 of FIG. 11 is similar to section 14 shown in FIG. 1, and differs from it with respect to elements 120 (as shown in FIG. 11) and 20 (as shown in FIG. 5). The same reference numbers are used for the identical elements.

The light housing 120 comprises an array of LED light emitters E' (as best shown in FIG. 12) that includes one or more LED light emitters VL (two VL LEDs in the example of FIG. 12) whose function is to irradiate visible light which is detectable by the video camera. Array E' also includes one or more LED light emitters CL (22 CL LEDs, in the example of FIG. 12) whose function is to irradiate light at a wavelength that can cure an adhesive used for affixing the bracket to the tooth surface. The array E' may includes 4 VL LEDs plus 20 CL LEDs, or any other combination of VL and CL LEDs, that can provide illumination sufficient for the camera to capture an image, and curing light with sufficient energy for the light-sensitive adhesive in use to be cured by that curing light.

The use of light sensitive adhesive to affix a bracket to tooth surface per se is generally known by itself, and does not form a part of the present invention. As is well known, the light-sensitive adhesives are usually sensitive to light having a specific wavelength, such as a blue light wavelength. Thus, the CL LED's are designed to emit light at the proper wavelengths for curing.

As is also well known, the duration of the exposure to the curing light for proper curing of the adhesive depends upon the type and thickness of the adhesive layer put on the bracket, as well as the power and characteristics of the curing light from the curing light sources. Thus, it is possible to generate curing light sufficient for producing initial tacking between the bracket and the surface of a tooth, as needed for example, for removing residual adhesive material. It is also possible to generate curing light sufficient for producing the complete bonding between the bracket and the tooth surface.

As shown in FIG. 13, a module M' controls the operation of the appliance 112. The module M' also includes the elements of the monitoring station M as shown in FIG. 1 (not shown in FIG. 13). The VL LEDs that illuminate visible light are controlled by the VL control unit. The CL LEDs that generate curing light are controlled by the CL control unit.

The operation of the VL LEDs is synchronized with the operation of the video camera, as described above with reference to FIGS. 1 to 5. The operator of the appliance (e.g.

the orthodontic) can manually control the operation of the CL LEDs in the following manner. The monitoring station M', in real time, shows on its screen both the changing image as the appliance is being manipulated and the position information which guides the user. When the current position of the bracket on the tooth surface coincides with its desired position, the operator is able to activate the CL control, unit to generate curing light for tacking the bracket to the surface or for complete bonding. Alternatively, the operation of the CL LEDs can be synchronized with the operation of the monitoring station, such that the activating signal for the CL control unit is generated automatically. In the case of generating a first curing light burst for tacking purposes, the operator is able to activate the CL control unit to generate a second curing light burst for producing complete bonding. The operator can manually activate the CL control unit, for example, by pressing an ON/OFF push button, which may be a part of the band-held wand 112 or the module M'. Alternatively, the push button may be a part of an external unit such as a pedal, connected to the module M'. Furthermore, the operation of the CL LEDs can be further synchronized with the operation of the monitoring station, to allow the operator to monitor the position of the appliance while the curing light is irradiated. This can guide the operator to generate the curing light in the appropriate direction only.

FIGS. 14 to 17 relate to yet another positioning appliance according to the invention, in which the illuminating system includes light sources only for the irradiation of light at a wavelength that can cure an adhesive used for affixing the bracket to the tooth surface. In this case too, the illuminating system can be implemented in the direct-view embodiment as well as in the Reflector-view embodiment of the positioning appliance.

Figure 14:
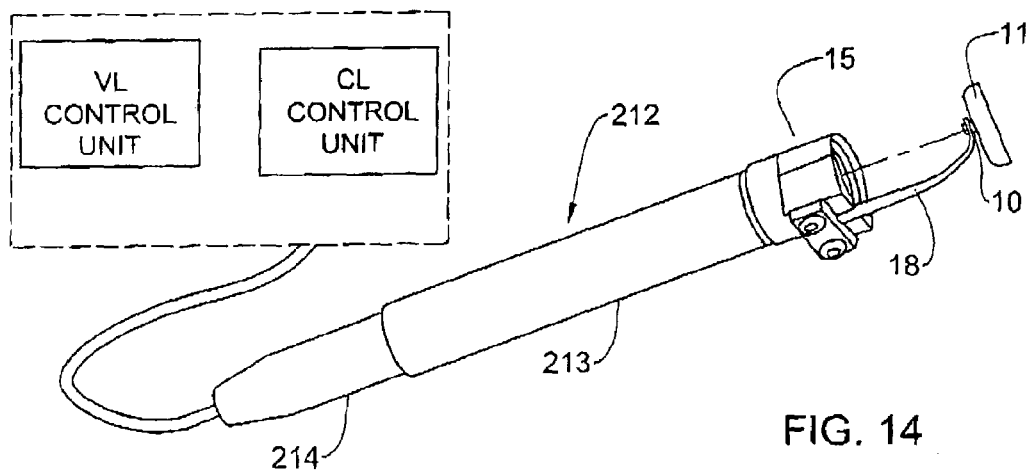
FIG. 14 illustrates in perspective a direct-view appliance in accordance with an embodiment of the invention adapted to position an orthodontic bracket or other implement on a tooth surface, the appliance being capable of affixing the bracket or other implement to the tooth surface.
Figure 15:
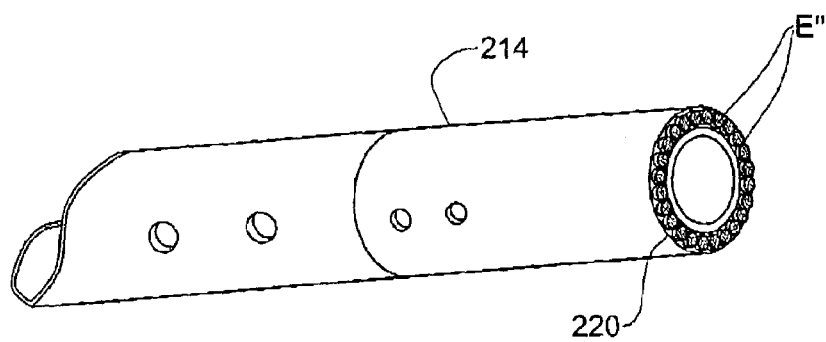
FIG. 15 is a longitudinal section of the light source section according to the appliance of FIG. 14, showing the light source elements.
Figure 16:
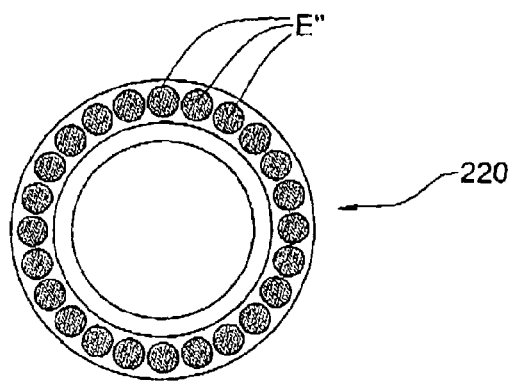
FIG. 16 is a front view of the light source section of FIG. 14.

FIG. 14 shows in perspective a direct-view appliance 212 adapted to position an orthodontic bracket or other implement on a tooth surface. Appliance 212 is in the form of a hand-held tubular wand composed of a protective sleeve section 213 and a light source section 214 telescoped into the sleeve section. As best shown in FIGS. 15 and 16, the light source section 214 includes a light housing 220 that comprises an array of LED light emitters E". The array E" includes one or more LED light emitters CL (24 CL LEDs, in the example of FIG. 16) whose function is to irradiate light at a wavelength that can cure an adhesive used for affixing the bracket to the tooth surface. The appliance 212 resembles appliances 12 and 112 in that it includes substantially the same sleeve section 13 (and specifically, includes the same optic line, denoted x in FIG. 1 and FIG. 6). The appliance 212 differs from appliances 12 and 112 in that it does not include a video camera or any other kind of camera.

The direction in which the curing light hits the bracket and its surroundings affects the amount of energy that can be absorbed by the light-sensitive adhesive, and consequently can cause bonding strength losses. To overcome this undesired outcome, the optic arrangement of the appliances according to the invention is designed to provide sufficient energy that reaches the vicinity of the bracket. With respect to FIGS. 13 and 14, it should be noted that the curing light is produced at the front surface of sections 114 and 214 (respectively), which is telescoped into the sleeve sections 113 and 213 (respectively), wherein the curing process takes place at the vicinity of the bracket 10 and the surface of tooth 11. The distance between the front surface of the light housing, from which the light is emitted, and the bracket is fixed, by the curved finger (element 18 in FIG. 1 or alternatively, element 28 in FIG. 6). Thus, the light emerging from the light housing impinges onto the bracket and the tooth's surface such that the whole area in the vicinity of the bracket is lightened. Thus, the curing light may be absorbed by the sensitive adhesive along the bracket circumference. In the case of a bracket that has one or more openings shaped in its base (i.e. the bracket face that faces the tooth surface), the adhesive material may receive the curing light through these openings. By that, the invention is not limited to be used with only a specific kind of bracket, and can be used with a diversity of brackets, of different sizes and shapes.

The desired wavelength of the curing light emitted from the CL LEDs can be obtained, for example, by utilizing an array of light sources, which emits light at the desired wave, as shown in FIGS. 12 and 16. Alternatively, the array E' can generate the needed curing light by utilizing a visible light source (such as VL LEDs) and appropriate filters which transmit the light component having the desired wavelength and block all other light components.

It should be noted that the appliance according to the invention is not limited to a specific kind of light-sensitive adhesive. In particular, it is possible to use the appliance with dual cure adhesives that require curing light for the initial tacking and for the initiation of a chemical process to achieve the complete bonding. It should also be noted that the appliance according to the invention could be used with chemical adhesives, which are cured by themselves without the need for curing light. The use of chemical adhesives can be practiced with the appliance 12 described in FIGS. 1 to 10 (i.e. a positioning appliance which includes a camera) and also with the appliance 112 described in FIGS. 11 to 13 (i.e. a positioning appliance which includes a camera and curing light source, without the need to activate the curing light source).

The embodiments of the invention shown in FIGS. 1 to 13 utilize a video camera. It should be noted that the positioning appliance according to the invention is not bound by this specific embodiment. Thus, by way of a non-limiting example, the appliance can be used with other types of cameras, such as infrared, ultra-violet, or X-ray camera, all as required and appropriate. It should be noted that when utilizing the appliance with types of camera other than a video camera, only a curing light source may be used (i.e. only light sources CL as shown in FIG. 12), as it is not necessary to irradiate the bracket and the tooth surface with additional radiation.

While there has been shown and disclosed preferred embodiments of a positioning appliance in accordance with the invention, it will be appreciated that many changes may be made therein without departing from the spirit of the invention.

The invention claimed is:

1. A positioning appliance adapted to facilitate an orthodontics procedure in which a bracket or other orthodontic component is placed at a desired site on the surface of a tooth and affixed thereto, said appliance comprising:
    A. a hand-held tubular wand having a protective sleeve section and a camera section telescoped in the sleeve section;
    B. a window mounted at the front end of the sleeve section and a finger projecting from said sleeve section, adapted to hold said bracket at a position abutting said tooth surface; and
    C. a camera housed in said camera section to capture through said window an image of said bracket on the surface of the tooth.

2. An appliance as set forth in claim 1, further including a lens housed in said camera section to focus the image on the camera.

3. An appliance as in claim 1, in which said camera section further includes a light source.

4. An appliance as in claim 3, in which said light source irradiates curing light at a wavelength that can cure an adhesive used for affixing said bracket or other orthodontic component to said surface of a tooth.

5. An appliance as in claim 4, wherein said light source includes two or more light emitting diodes, in which:
   one or more of said light emitting diodes are capable of irradiates light at a wavelength detectable by said camera; and
   one or more of said light emitting diodes are capable of irradiates curing light at a wavelength that can cure an adhesive used for affixing said bracket or other orthodontic component to said surface of a tooth.

6. An appliance as in claim 3 in which said light sources emits light at a desired wavelength.

7. An appliance as in claim 3 in which said light sources generate said curing light by utilizing visible light source and appropriate filters which transmit the light component having the desired wavelength and block all other light components.

8. An appliance as in claim 3 wherein said curing light affects said adhesive to produce initial tacking between said bracket or other orthodontic component to said desired site on the surface of a tooth.

9. An appliance as in claim 3 wherein said light affects said adhesive to produce substantially complete bonding between said bracket or other orthodontic component to said desired site on the surface of a tooth.

10. An appliance as in claim 3, in which said camera is a video camera and said light source projecting a beam to illuminate the bracket and the tooth surface whereby the video camera then generates a clear video image thereof.

11. An appliance as in claim 10, in which the video image yielded by the camera section is conveyed to an external video monitor whose screen displays the video image whereby a user of the appliance by observing the display can see the position of the bracket on the tooth surface as the appliance is being manipulated.

12. An appliance as in claim 11, in which also presented on the monitor display is information to guide the user.

13. An appliance as in claim 1, further comprising two or more light sources in which:
   one or more of said light sources are capable of irradiates light at a wavelength detectable by said camera; and
   one or more of said light sources are capable of irradiates curing light at a wavelength that can cure an adhesive used for affixing said bracket or other orthodontic component to said surface of a tooth.

14. An appliance as in claim 1, in which the finger is shaped to hold the bracket against the tooth surface in alignment with an optical axis coaxial with the tubular sleeve section.

15. An appliance as in claim 1, in which the finger is shaped to hold the bracket against a tooth surface parallel to an optical axis coaxial with tubular sleeve section, further including a reflector mounted in front of the window to reflect an image from the bracket and the tooth surface toward the video camera.

16. An appliance as in claim 15, in which the reflector is formed by a plate having a specular surface mounted at a 45 degree angle in front of the window.

17. An appliance as set forth in claim 1, wherein the sleeve section is formed of a sterilizable metal tube whereby after each use of the appliance which brings it contact with a patient being treated, the sleeve section then can be separated from the camera section and sterilized so that the appliance is in condition for reuse.

18. An appliance as set forth in claim 17, in which the sleeve section is formed of stainless steel.

19. An appliance as set forth in claim 17, in which the sleeve section is formed of titanium.

20. An appliance as set forth in claim 17, in which the sleeve section is sterilizable in an autoclave where it is subjected to superheated steam.

21. An appliance as in claim 1, in which the window is mounted on a collar at the front end of the sleeve section, and the finger is attached to said collar and projects therefrom.

22. An appliance as in claim 21, in which the finger is shaped to hold the bracket to be placed on the tooth surface in front of the window mounted on the collar.

23. An appliance as in claim 21, in which the finger is shaped to hold the bracket on the tooth surface lying on a lateral axis at right angles to an optical axis coaxial with the sleeve section, a reflector being placed at the intersection of the lateral and optical axes to reflect an image of the bracket and tooth surface toward the camera section.

24. An appliance as in claim 1, in which said bracket is cross-slotted at its rear face, and said finger terminates in a tip shaped to engage a slot in said rear face.

25. An, appliance as in claim 24, in which the tip has a wedge shape that wedges into a slot in said cross-slotted face.

26. An appliance as in claim 24, in which the tip is in the shape of an arched wire that wedges into a slot in said cross-slotted face.

27. A positioning appliance adapted to facilitate an orthodontics procedure in which a bracket or other orthodontic component is placed at a desired site on the surface of a tooth and affixed thereto, said appliance comprising:
   A. a hand-held tubular wand having a protective sleeve section and a video camera section telescoped in the sleeve section;
   B. a window mounted at the front end of the sleeve section and a finger projecting from said sleeve section, adapted to hold said bracket at a position abutting said tooth surface;
   C. a video camera housed in said camera section to capture through said window an image of said bracket on the surface of the tooth;
   D. illuminating system housed in said camera section and configured to perform at least one of the following:
      irradiating the bracket and the tooth surface with light detectable by said camera; and
      irradiating light at a wavelength that can cure an adhesive used for affixing said bracket or other orthodontic component to said surface of a tooth.

28. An appliance as in claim 27 in which said illuminating system is configured to emit light at a desired wavelength.

29. An appliance as in claim 27 in which said illuminating system generate said curing light by utilizing visible light source and appropriate filters which transmit the light component having the desired wavelength and block all other light components.

30. An appliance as in claim 27, in which the video image yielded by the camera section is conveyed to an external video monitor whose screen displays the video image whereby a user of the appliance by observing the display can see the position of the bracket on the tooth surface as the appliance is being manipulated.

31. An appliance as in claim 30, in which also presented on the monitor display is information to guide the user.

32. An appliance as in claim 27, in which the finger is shaped to hold the bracket against the tooth surface in alignment with an optical axis coaxial with the tubular sleeve section.

33. An appliance as in claim 27, in which the finger is shaped to hold the bracket against a tooth surface parallel to an optical axis coaxial with tubular sleeve section, further including a reflector mounted in front of the window to reflect an image from the bracket and the tooth surface toward the video camera.

34. An appliance as in claim 33, in which the reflector is formed by a plate having a specular surface mounted at a 45 degree angle in front of the window.

35. An appliance as set forth in claim 27, wherein the sleeve section is formed of a sterilizable metal tube whereby after each use of the appliance which brings it contact with a patient being treated, the sleeve section then can be separated from the camera section and sterilized so that the appliance is in condition for reuse.

36. An appliance as set forth in claim 35, in which the sleeve section is formed of stainless steel.

37. An appliance as set forth in claim 35, in which the sleeve section is formed of titanium.

38. An appliance as set forth in claim 35, in which the sleeve section is sterilizable in an autoclave where it is subjected to superheated steam.

39. An appliance as in claim 27, in which the window is mounted on a collar at the front end of the sleeve section, and the finger is attached to said collar and projects therefrom.

40. An appliance as in claim 39, in which the finger is shaped to hold the bracket to be placed on the tooth surface in front of the window mounted on the collar.

41. An appliance as in claim 39, in which the finger is shaped to hold the bracket on the tooth surface lying on a lateral axis at right angles to an optical axis coaxial with the sleeve section, a reflector being placed at the intersection of the lateral and optical axes to reflect an image of the bracket and tooth surface toward the camera section.

42. An appliance as in claim 27, in which said bracket is cross-slotted at its rear face, and said finger terminates in a tip shaped to engage a slot in said rear face.

43. An appliance as in claim 42, in which the tip has a wedge shape that wedges into a slot in said cross-slotted face.

44. An appliance as in claim 42, in which the tip is in the shape of an arched wire that wedges into a slot in said cross-slotted face.

45. A positioning appliance adapted to facilitate an orthodontics procedure in which a bracket or other orthodontic component is placed at a desired site on the surface of a tooth and affixed thereto, said appliance comprising:
  A. a hand-held tubular wand having a protective sleeve section and a light source section telescoped in the sleeve section;
  B. a window mounted at the front end of the sleeve section and a finger projecting from said sleeve section, adapted to hold said bracket at a position abutting said tooth surface; and
  C. one or more light sources housed in said light source section, capable of irradiates light at a wavelength that can cure an adhesive used for affixing said bracket or other orthodontic component to said surface of a tooth.

46. An appliance as in claim 45 in which said light sources emit light at a desired wavelength.

47. An appliance as in claim 45 in which said light sources generate said curing light by utilizing visible light source and appropriate filters which transmit the light component having the desired wavelength and block all other light components.

\* \* \* \* \*